United States Patent [19]

Goerlach-Graw et al.

[11] Patent Number: 5,424,220
[45] Date of Patent: Jun. 13, 1995

[54] ANALYSIS ELEMENT AND METHOD FOR DETERMINATION OF AN ANALYTE IN A LIQUID SAMPLE

[75] Inventors: Ada Goerlach-Graw, Weisenheim am Sand; Ulrich Naegele, Weinheim; Hans-Erich Wilk, Einhausen; Reiner Graw, Weisenheim am Sand, all of Germany

[73] Assignee: Boehringer Mannheim GmbH, Mannheim, Germany

[21] Appl. No.: 10,985

[22] Filed: Jan. 29, 1993

[30] Foreign Application Priority Data

Jan. 31, 1992 [DE] Germany .................. 42 02 850.7

[51] Int. Cl.⁶ ............... G01N 33/543; G01N 33/558
[52] U.S. Cl. .................................. 436/568; 422/56; 422/57; 422/58; 435/7.92; 435/7.93; 435/7.94; 435/805; 435/810; 435/967; 435/970; 435/973; 436/164; 436/169; 436/514; 436/530; 436/805; 436/807; 436/810
[58] Field of Search .................. 422/56-58; 435/7.92, 7.93, 7.94, 805, 810, 967, 970, 973; 436/514, 518, 530, 164, 169, 805, 807, 810

[56] References Cited

U.S. PATENT DOCUMENTS

| | | | |
|---|---|---|---|
| 4,216,245 | 8/1980 | Johnson | 422/56 |
| 4,361,537 | 11/1982 | Deutsch et al. | 422/56 |
| 4,376,945 | 3/1983 | Hara et al. | 346/140 |
| 4,496,654 | 1/1985 | Katz et al. | 422/56 |
| 4,591,570 | 5/1986 | Chang | 436/570 |
| 4,853,325 | 8/1989 | Vodian et al. | 436/810 |
| 4,861,711 | 8/1989 | Friesen et al. | 436/514 |
| 4,877,745 | 10/1989 | Hayes et al. | 422/56 |
| 4,988,627 | 1/1991 | Smith-Lewis | 436/165 |
| 5,061,640 | 10/1991 | Tischer et al. | 436/518 |
| 5,089,420 | 2/1992 | Albarella et al. | 422/56 |
| 5,141,850 | 8/1992 | Cole et al. | 422/56 |

FOREIGN PATENT DOCUMENTS

| | | |
|---|---|---|
| 1101771 | 5/1981 | Canada . |
| 1187786 | 5/1985 | Canada . |
| 0061167 | 9/1982 | European Pat. Off. . |
| 0119573 | 9/1984 | European Pat. Off. . |
| 0192428 | 8/1986 | European Pat. Off. . |
| 0212642 | 3/1987 | European Pat. Off. . |
| 0260929 | 3/1988 | European Pat. Off. . |
| 0268237 | 5/1988 | European Pat. Off. . |
| 0291194 | 11/1988 | European Pat. Off. . |
| 0299428 | 1/1989 | European Pat. Off. . |
| 0344578 | 12/1989 | European Pat. Off. . |
| 0408078 | 1/1991 | European Pat. Off. . |
| 0469444A1 | 2/1992 | European Pat. Off. . |
| 0469445A1 | 2/1992 | European Pat. Off. . |
| 2355290 | 1/1978 | France . |
| 3346795 | 7/1985 | Germany . |
| 3445816 | 6/1986 | Germany . |
| 4037724A1 | 6/1991 | Germany . |
| 1526708 | 9/1978 | United Kingdom . |
| 2239313 | 6/1991 | United Kingdom . |
| WO84/04171 | 10/1984 | WIPO . |
| WO91/15769 | 10/1991 | WIPO . |

*Primary Examiner*—Toni R. Scheiner
*Assistant Examiner*—Christopher L. Chin
*Attorney, Agent, or Firm*—Nikaido, Marmelstein, Murray & Oram

[57] ABSTRACT

The invention addresses an analysis element for the determination of an analyte according to the principle of a heterogeneous immunoassay. Said analysis element is made of a chromatographic porous carrier material and has a reaction zone, at least two detection zones and absorptive zones following said detection zones. The reaction zone contains analyte-specific and labelled binding partners which are present in a number of soluble compartments which are close together, but nevertheless spatially separated. The detection zones are adjacent to the reaction zones and contain an immobilized binding reagent for one of the binding partners present in the reaction zone. At least one detection zone contains a binding reagent for the analyte-specific unlabelled binding partner.

20 Claims, 1 Drawing Sheet

ANALYSIS ELEMENT AND METHOD FOR DETERMINATION OF AN ANALYTE IN A LIQUID SAMPLE

The invention addresses an analysis element for the determination of an analyte in a sample liquid as known from heterogeneous immunoassays. Said analysis element is made of a porous capillary-active carrier material and has a reaction zone and at least two detection zones. Further, the invention relates to a process for the determination of an analyte in a sample liquid according to the principle of an heterogeneous immunoassay using said analysis element.

In medical diagnostics, the number of substances to be determined in physiological sample liquids has grown tremendously. Immunological detection methods have gained increasingly more importance in the determination of these substances or analytes. Particular prominence is given to heterogeneous immunoassays where, usually, an analyte-specific binding partner which exhibits bioaffinity is bound to a solid phase. A general distinction is made between competitive immunoassays and sandwich immunoassays.

In competitive immunoassays, a predetermined amount of a labelled analyte derivative competes with the analyte molecules to be determined for the binding site of the binding partner which is bound to a solid phase. After a certain incubation period, the non-bound material is washed out and the amount of labelled analyte derivative which is present in the bound or the free phase is determined as a measure for the amount of analyte present.

In sandwich immunoassays, the analyte is, as a rule, first bound to the analyte-specific binding partner which in turn is bound to the solid phase. Then, a second analyte-specific binding partner carrying a measurable label is added in excess. After all non-bound material is washed out, the amount of labelled reagent present at the bound phase is determined as a measure for the amount of analyte.

In the recent past, heterogeneous immunoassays have been proposed which are provided on test carriers made of a porous or fibrous material. Test carriers of this kind feature chromatographic properties which serve to separate bound from non-bound labelled reagent. It was also an object of the invention to integrate all binding partners necessary for the heterogeneous detection reaction on such test carriers thus reducing the number of reagent metering steps (fully integrated analysis elements). U.S. Pat. No. 4,361,537 EP-A-0 291 194 or EP-A-0 186 799 describe chromatographic test strips having an analyte application zone and a detection zone which are separated from one another on the test carrier. The detection zone contains an immobilized binding partner. This binding partner can be directly specific for the analyte (e.g. an immobilized antibody) or for an analyte-specific binding partner (e.g. streptavidin which specifically binds biotinylated analyte antibodies or biotinylated analyte derivatives). The remaining binding partners necessary for the immunoassay are successively applied onto discrete zones provided between the application zone and the detection zone so as to avoid a premature interaction between the reagents prior to adding the analyte. Especially in competitive test, such an interaction, e.g. between labelled analyte derivative and the binding sites of the analyte-specific binding partner must be prevented until the analyte is also able to participate in this competitive reaction.

In order to check whether the labelled binding partners actually travel toward the detection zone during chromatography, i.e. whether or not the labelling is still functioning, it has also been proposed to provide a second detection zone behind the first detection zone. Said second detection zone acts as a control zone where the antibodies to the free labelled binding partners, for example, are immobilized. After passing the first detetion zone, the free labelled binding partner is bound in this control zone thus allowing a positive control of the reaction.

A drawback of the chromatographic test strips described in the above quoted specifications is that due to the serial arrangement of the various immune reagents, it is not possible to mix the reagent, which are successively dissolved in the flowing liquid, such that a completely homogeneous mixture is obtained. The concentration ratios at and behind the chromatography front constantly change as do, consequently, the binding balances of the different binding partners. Such test strips are, hence, only suitable for use in qualitative and semiquantitative tests. Further, the problem of having a positive reaction control has not been solved to satisfaction since the labelled binding partners, prior to reaching the control zone, must first pass the detection zone where they can be stopped as a consequence of non-specific interactions. The control zone only allows the detection of those labelled binding partners that are free and have not been bound or captured in the detection zone. This, however, occurs time delayed with respect to the actual result of the analysis. A quantitative correction of the result with the aid of such control zones is not possible.

It can be said that measurements with test strips of this kind are generally relatively inaccurate and require extended chromatography times. A quantitative check of the test result is not possible and there is no satisfactory control of the function of the labelled components.

It is hence, an object of the present invention to eliminate the disadvantages of analysis elements known in prior art and provide a fully integrated chromatographic analysis element which produces more accurate results in a shorter period of time. Moreover, said analysis element should allow checking and correcting of the results while simultaneously and reliably controlling the functioning of the labelled binding partner.

This object is accomplished with an analysis element as characterized in the claims.

Subject matter of the invention is an analysis element for measuring an analyte according to the principle of a heterogeneous immunoassay. Said analysis element is made of a chromatographic carrier material and has a reaction zone, at least two detection zones which are spatially separated from the reaction zone, and absorption zones provided adjacent to the detection zone at the side remote from the reaction zone. Said analysis element is characterized in that analyte-specific and labelled binding partners are provided on the reaction zone in a number of compartments which are close together, but nevertheless spatially sparated; further, in that each detection zone contains a binding reagent for a binding partner present on the reaction zone, said binding reagent being immobilized, whereby at least one detection zone contains a binding reagent for the analyte-specific, non-labelled binding partner and in that the detection zones are arranged around the reaction zone so that each zone is located next to the reaction zone.

In the test element, the porous capillary-active carrier material is present as a surface matrix. The surface can, for example, be configured as a square, a rectangle or a circle. Also possible is a surface segment in the form of a test strip. Any porous material which, due to capillary forces, is capable of transporting a liquid and reagent dissolved therein parallel to the surface of the carrier material and which does not negatively interact with the reagents used may serve as a material for the absorbent matrix. Such porous carrier materials are known to the expert. Possible materials include, for example, paper, cellulose, nitrocelloluse, pressed fibers, including glass fibers, sintered glass, ceramic or plastic materials having porous or fibrous structure and sufficient hydrophilic properties. A particularly avantageous material is nitrocellulose.

The selection of the pore size of the material depends upon the respective reaction conditions. Suitable pores sizes range between 0.1–5 $\mu$m, preferably 0.45–1 $\mu$m. An advantageous matrix thickness ranges between 50 and 250 $\mu$m.

The following binding partners are necessary for the complete heterogeneous immune reaction:

The first binding partner is immobilized on the membrane where it is permanently fixed to the carrier. Said first binding partner is not analyte-specific but specific for a second binding partner (immobilized, non-analyte-specific partner). A second binding partner specifically binds to the first binding partner and is analyte-specific (analyte-specific binding partner) but is not labelled. Said binding partner is present in a non-immobilized form. i.e. it is freely soluble once it comes into contact with a liquid. When it comes into contact with the first immobilized binding partner, it is first bound to the latter and only then immobilized. A third binding partner is the labelled reaction component (labelled binding partner) which is used to determine the result. This binding partner is not immobilized either, i.e. it is fixed on the carrier in a soluble manner.

The expert is familiar with methods of labelling and detecting components of immune reactions. Direct labellings such as dye molecules, metal brine, fluorophores, luminophores or, for example, phycobiliproteins or fluorescent latex, which can be detected without additional reagents, have proven well for this purpose. The use of fluorescent labels is particularly advantageous.

The third labelled binding partner depends upon the immunological test principle which is applied. If, for example, the analyte is an antigen, the free labelled binding partner can, in a competitive immunoassay, be a labelled antigen which corresponds to said antigen. In this case, said second binding partner is an antibody capable of binding to said first binding partner. The labelled binding partner and the antigen compete for the binding sites at the second binding partner, the quantity of bound labelled analyte analog being a measure for the concentration of the analyte.

In an immunoassay according to the sandwich principle, the free, labelled binding partner can be a labelled analyte-specific antibody. The second binding partner and the labelled binding partner then bind the analyte antigen at different epitopes. The quantity of bound labelled binding partner is a measure for the concentration of the analyte. The terms antigen and antibody are used interchangeably in the above description.

A preferred first binding partner (immobilized and not analyte-specific), can be streptavidin (or avidin) which specifically binds the second analyte-specific binding partner due to the conjugation thereof to a biotin molecule. Also possible is any other specific binding combination such as sugar/lectin, complementary nucleotide sequences, enzyme/cofactor, antibody/antigen and the like, all of which are known to the expert.

On its surface, the capillary-active carrier is provided with at least three zones forming discrete surfaces. Said zones are spatially separated from one another and, since they contain immune reagents, are referred to as functional zones.

The preferred position of the reaction zone is in the center of the carrier surface. The reaction zone is characterized in that it contains, in a common delimited area, the two binding partners, i.e. analyte-specific binding partner and the labelled binding partner, in the form of numerous compartments which are close together, but nevertheless spatially separated on one surface.

The preferred form of the reaction zone is a circle, however, other forms, e.g. the rectangle of a test strip, are also possible. The surface area of the reaction zone essentially depends upon the quantity of immune reagent to be applied. In a preferred manner, the area of the reaction zone is part of the carrier material itself. However, it is also possible to provide an additional capillary-active layer on the carrier material in the area of the reaction zone, said layer being in contact with said carrier material so as to allow liquid to be transported and containing all immune reagents.

In comparison to the dimensions of the reaction zone, the term "3compartment" designates a small, discrete segment containing one type of reagent. A compartment may be one dot or several overlapping dots or a line.

The compartments are spatially separated from each other on the reaction zone by spacing them apart at very small distances. In a preferred manner, compartments with different reagents alternate, i.e. adjacent compartments have different reagents. For practical reasons, it is recommended to have a regularly alternating pattern where compartments with different reagents are cyclically repeated in one or even both surface directions thus producing a regular pattern of lines or dots. In exceptions, it may also be suitable to have an alternating but not cyclically repeated pattern. In an ideal manner, the distance between the compartments should be indefinitely small. On the other hand, when dry, the compartments with the different reagents should not contact one another.

It has proven to be practical to provide a distance of 10 $\mu$m to 1 mm between the outer limits of the individual compartments, preferably a distance ranging between 30 $\mu$m and 250 $\mu$m, and particularly preferred a distance ranging between 40 $\mu$m and 100 $\mu$m. Advantageously, the width of the compartment lines or the diameter of the compartment dots should be less than 2 mm and preferably ranges between 50 $\mu$m and 1 mm. This way of formatting and arranging the compartments is hereinafter also referred to as micro-compartmentalization.

The reagents contained in the compartments of the reaction zone are non-immobilized, i.e. when dry, they do adhere to or in the surface of the carrier portion forming a compartment but are easily dissolved once a liquid is added onto the reaction zone ("soluble compartment"). It is recommended to use those materials as carrier materials whose surface shows little or no non-specific interaction with the analyte or the immune reagents present in the soluble compartments. Examples include modified nylon membranes such as LOPROYNE TM nylon membranes or other hydrophilic membranes such as DURAPORE TM hydrophilic Durapore ® manufactured by Millipore.

The procedure used for the application of immune reagents in the form of compartments must be suitable to apply several different immune reagents onto a porous membrane in segments that are close together, but nevertheless spatially separated. Application must occur in a selected and reproducible manner with different reagents being present next to each other on a smallest possible space where they are partly elutable and partly immobilized.

To date, this method of applying immune reagents has not yet been described.

A great number of different printing techniques has proven to be suitable. These techniques include screen printing, different variants of ink-jet printing known from computer technology, matrix printing techniques, brushing techniques such as airbrushing, "charged drop" printing techniques and various others.

In screen printing, a first component is applied onto the carrier material through a fine-mesh screen, the screen is then moved and a second component and, optionally, additional components are applied into the gaps of the first screen. The distances between the individual compartments are then at the upper acceptance limit of the present invention.

The application of immune reagents with the matrix printing technique is again more suitable for those cases which do not require a particularly small distance between the compartments.

A high-precision metering pump applies reagent liquid onto the membrane through an extremely small hollow needle with internal diameter 0.05 to 1 mm.

The line thickness depends on how fast the needle is moved across the membrane or how fast the membrane is moved underneath the needle. In a preferred manner, reagent is applied with the opening of the needle being upwardly directed while the membrane is moved over the opening.

More preferred methods in accordance with the invention are those methods which reduce the distance between the compartments. They include, for example, the application of immune reagents using the so-called air-brush technique. This is a continuous spraying technique where microdroplets which are enveloped in a gas flow are applied onto a surface, preferably in the form of lines. The gas flow serves to redirect and position the jet of microdroplets. This method is known from the application of analyte solutions onto the starting line of plates used in thin layer chromatography.

It turned out that commercially available instruments (e.g. the CAMAG DC-Probenautomat III) are also suitable to apply different immune reagents in micro-compartments onto a porous matrix. The typical size of the microdroplets ranges between 1 nl and 1000 nl, preferably less than 100 nl. These micro-droplets are then applied onto the reaction zone of the analysis element in a dot or line pattern, preferably such that compatible and non-compatible reagents alternate with one another. The density of the lines or dots depends on the absorptive capacity of the carrier material and the preferred size of the droplets, the latter ranging between 10 and 1000 lines per $cm^2$, or 100 and 10,000 droplets per $cm^2$.

Even more advantageous in accordance with invention are ink-jet techniques which have originally been developed for computer printers. These processes allow the application of even smaller portions of reagent liquid. Among the various methods of this technology, particular preference is attached to the so-called bubble-jet technique. Ink-jet techniques are divided into continuous and discontinuous techniques. Both groups are suitable for the invention.

EP-A-119 573 and EP-A-268 237 (U.S. Pat. No. 4,877,745) describe the use of two particular variants of the discontinuous ink-jet technique for the application of a reagent on a spatially delimited surface area. Such a delimited area can, for example, have the form of a plus or minus sign so as to produce a distinct result or make the result more understandable for a non-expert: or said area may serve to allow a direct comparison between a reagent-coated and a reagent-free segment. As regards the ink-jet technology, reference is made to the documents quoted hereabove. The ink-jet technology is distinguished in that very minute quantities of a liquid can be applied onto a carrier layer with a very high degree of precision. Precision is required for both the exact positioning of the dot created by the reagent droplet on the carrier layer and the reagent volume. The droplets are successively ejected at very high frequency.

With the various ink-jet techniques, it is possible to apply different reagents onto porous membranes within a very small space in the form of compartments which are close together, but nevertheless spatially separated.

For the preparation of the analysis element in accordance with the invention, the typical quantity of reagent liquid ejected by the ink-jet nozzle ranges between 2 and 2000 nl, the preferred volume ranging between 100 and 800 nl. The surface of a dot created by such a quantity on the carrier layer greatly depends on the reagent liquid and the carrier layer. It ranges approximately between 3,000 $\mu m^2$ and 0.1 $mm^2$, preferably between 500 $\mu m^2$ and 0.2 $mm^2$. The quantities of reagent liquid are typically ejected at a frequency of more than 1,000 $s^{-1}$, preferably between 1,000 and 200,000 $s^{-1}$. Further details are given in the German patent specification DE-A-4024544.

The above described documents EP-A-119 573 and EP-A-268 237 describe only the use of particular variants of the ink-jet technique for the application of reagents on larger surfaces where, according to one variant, the volume is mechanically compressed in the nozzle chamber and according to another variant, compressed by means of piezo-electricity in order to eject a droplet.

It has now been found that among the available ink-jet techniques, the bubble jet technique which has hitherto not been described for the application of reagents has also proven to be advantageous for the manufacture of an analysis element in accordance with the invention.

In the bubble jet technique which is also known from computer printers, a partial volume of the liquid is briefly evaporated in the nozzle chamber and expands so as to eject a quantity of liquid through the nozzle. This technique does not involve any mechanically moved parts and thus provides a high degree of reliability. Further, the available viscosity range for the liquid is extended. Although the liquid is heated up very high in the nozzle chamber, it has surprisingly been found that there is practically no significant damage done to the immune reagents contained in the liquid. For a compartmentalization of the various reagents on the analysis element of the invention with the aid of ink jet techniques, it is preferable to use a multi-channel printing head as has been developed for color printing, for example. The printing head can be positioned in both directions of surface of the multi-functional layer with the aid of a X-Y driving mechanism which is controlled by a control unit. Apart therefrom, it is also possible to use the constructive features known in ink jet techniques, particularly in the bubble jet technique. These features have been described in the literature. Further details are also given in German patent application DE-A-4024545.

The reaction zone of the analysis element of the invention is surrounded by at least two detection zones. A detection zone is understood to be a spatially delimited area which is separated from the reaction zone by liquid-transporting segment of the carrier material. In said detection zone, there is present a binding reagent specific for one of the immune reagents which is transferred out of the reaction zone in a chromatographic procedure and the labelled component of the immune reaction is detected. The binding reagent is immobilized by means of processes that are known to the expert, e.g. covalent binding or adsoprtion at or in the carrier material.

A specific binding reagent is understood to be a binding reagent for the analyte-specific binding partner (and the immune complexes thereof) or a binding reagent which specifically binds the labelled binding partner. Binding reagents that bind an analyte-specific binding partners include, for example, streptavidin. The latter, in the form or polystreptavidin or TRSA-streptavidin, is in a printing process immobilized on the detection zone, covering said zone completely and binds biotinylated antibodies or biotinylated analyte derivatives very quickly and effectively (cf. EP-A-0 344 578). Other binding partners with bioaffinity include lectin/-sugar, complementary nucleotide sequences, enzyme/-cofactor, antibody/antigen and the like.

A binding reagent which binds a labelled binding partner can, for example, be an immobilized antibody which is directed against the free labelled binding partners.

The actual result is measured in a detection zone ("measuring-detection zone") which contains an immobilized binding reagent to the analyte-specific binding partner, i.e. the number of analyte-specific binding combinations linked to the labelled reagent serves in this zone as a measure for the amount of analyte contained in the sample liquid.

In the detection which contains a binding reagent for a free labelled binding partner, the amount of labelled binding partner which has travelled a certain distance is detected. Such a zone may also be referred to as a "control-detection zone" since it allows controlling both the chromatographic travel of the labelled binding partner out of the reaction zone and its proper functioning.

An essential feature of the invention is that two or more detection zones are arranged around the reaction zone in such a manner that are all located next to the latter. This excludes an arrangement of the type reaction zone - detection zone - detection zone in one line. Each detection zone must, hence, be separated from a reaction zone only by the capillary-active carrier zone. It is particularly advantageous if all detection zones are spaced apart from the reaction zone at the same distance. The surface of a test strip with a central reaction zone can, for example, be provided with detection zones, with one such zone being located on each side of said central reaction zone and both being preferably provided at the same distance from said reaction zone.

More than two detection zones can be provided on the surface of a carrier material so as to be concentrically arranged around the reaction zone in different directions. If all detection zones are provided at the same distance from the reaction zone, this arrangement will produce a circle.

At least one of the at least two detection zones arranged around the reaction zone is a measuring detection zone containing a binding reagent for the analyte-specific binding partner and its complexes. Additional detection zones are present as one or several measuring-detection zones and/or one or several control-detection zones containing immobilized binding reagent for the labelled binding partner.

Behind the detection zones, i.e. at the side facing away from the reaction zone, there is provided the absorptive portion of the carrier material. The purpose of the absorptive portion of the carrier material is to absorb, by means of capillary forces, sample liquid, wash solution und reagent that has not been fixed in the detection zone. This function of the carrier material can advantageously be supported by providing in the absorptive portion an additional material having particular absorptive capacities. Whatman 3 MM paper has proven well for this purpose.

Further, another subject matter of the invention is a process for the determination of an analyte in a sample liquid according to the principle of an heterogeneous immunoassay where the analysis element of the invention is used. This process is characterized in that the sample solution is applied onto the reaction zone, then wash solution is applied onto the reaction zone to transfer dissolved reagents, in a chromatographic process, out of the reaction zone in direction toward the detection zones; further, in that the labelled reaction components bound in said detection zones are measured and in that the measurements in the various detection zones are used for the qualitative control and/or quantitative improvement of an analyte determination.

For the determination of an analyte on the analysis element of the invention, a sample solution containing the analyte to be determined is applied onto the reaction zone. In a preferred manner, the solution is applied onto the center of this zone and the volume dispensed should be sufficient to cover the entire zone with liquid. Since the reagents are applied in micro-compartments, they are quickly and uniformly distributed upon addition of sample liquid and quickly react in a homogeneous reaction. Once the reaction of the binding partners is completed, a wash solution is preferably added onto the center of the reaction zone causing the dissolved reagents and immune complexes to move in a chromatographic process essentially radially out of the reaction zone in all directions. When a test strip is used, the reagents are, due to the outer limits of the strip, transported toward the outside in both longitudinal directions of the strip and in an essentially uniform manner. Conventional buffering solutions are used as wash solutions for immune reagents.

As soon as the binding partners reach the detection zones which contain the corresponding immobilized binding reagents, they are captured while the remaining reagents pass the detection zone so as to be absorbed in the absorptive zone.

At least one detection zone contains immobilized binding reagents for the analyte-specific binding partner so that this measuring-detection zone produces a first measurement of the quantity of analyte contained in the sample solution by measuring the immobilized label. If the analysis element has one or several other measuring-detection zones, one or several other measurements are produced which can be compared to the first measurement or can be compared to each other. The great advantage of such double- or multi-measurements with the analysis element of the invention is that most of the parameters of the test procedure are identical. In the reaction zone, for example, the reaction partners form a homogeneous solution which is uniformly distributed radially toward the outside so that the initial concentration of the reaction partners is identical for each measurement. Essentially, only those inhomogeneities affect the different measurements which are generated while the reagents travel from the detection zone to the different measuring-detection zones. However, these can be easily tracked down in double or triple measurements on different measuring-detection zones thus producing a more exact measurement.

The provision of two or more discrete but identical measuring-detection zones further increases the accuracy of the analyte determination. It is possible to measure different measuring-detection zones simultaneously at different wavelengths. This is particularly appreciated if components of the analyte solution interfere with the measurement in the measuring-detection zone. Many serum constituents, for example, which bind non-specifically in the measuring-detection zone have an elevated fluorescence background. Interferences of this kind can be detected in a measurement with two measuring-detection zones at two different wavelengths to be then mathematically eliminated.

The provision of one or several other control-detection zones in the analysis element in addition to the one or several measuring-detection zones further increases the reliability and accuracy of the measurement. A control-detection zone in accordance with the invention also indicates the movement of free labelled binding partners from the reaction zone to the detection zone. Said zone also indicates the extent to which the labelling system of these binding partners is still in function, i.e. the extent to which the antibodies, fluorophores or enzymes (in the case of enzyme labels) are damaged, e.g. by aging. The actual values obtained in a control-detection zone can be compared to a theoretical reference value to thus correct the result obtained in the measuring-detection zone with a corresponding factor. The advantage of the analysis element of the invention is that this control is carried out independently from and simultaneously with the determination of the analyte. Since the liquid does not have to pass another zone prior to reaching the control-detection zone, the result is not distorted in any way. Also, there is no time delay between the measurement of the analyte and the qualitative confirmation of the result.

The analysis element of the invention produces a quick and very accurate result.

When adding the sample liquid onto the reaction zone, the reagents applied in compartments are uniformly dissolved and qickly react in a very homogeneous reaction. The distances to be covered by the reagent during their chromatographic movement toward the detection zones are very short which accounts for a rapid and accurate test procedure. A first result with a concomitant positive reaction control can be obtained within 10–300 seconds. The provision of several discrete detection zones on one analysis element further increases the accuracy of the result. The simultaneous evaluation of different detection zones on an automated analyzer produces a very precise and corrected result without additional time being required.

The drawings are examples describing embodiments of the analysis element:

FIG. 1 shows a test strip with a strip-like carrier (1). In its center, the carrier is provided with a reaction zone (2) (serves also as a sample application zone). The streptavidin-coated measuring-detection zones (3) are arranged such that each such zone is spaced apart from the reaction zone at the same distance and connected to the reaction zone (2) via the capillary-active material of the carrier matrix. The area of the carrier matrix behind the detection zone (3) serves as an absorptive segment (4) for excess liquid and its effect can be supported by providing additional absorptive material (5).

EXAMPLE 1

Competitive immunoassay for T4

Reagents

Figure 1:
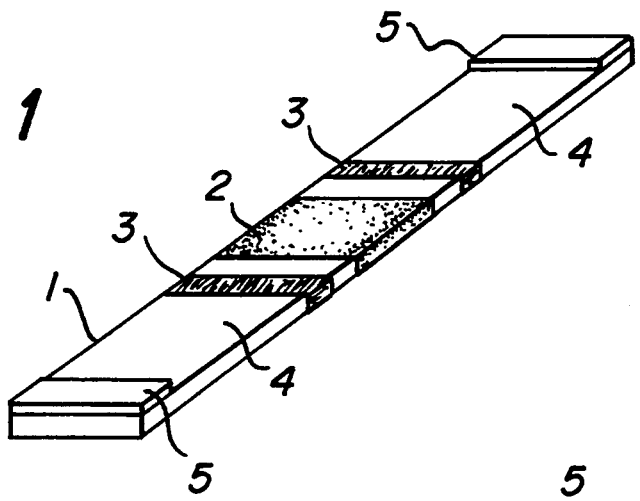
Figure 2:
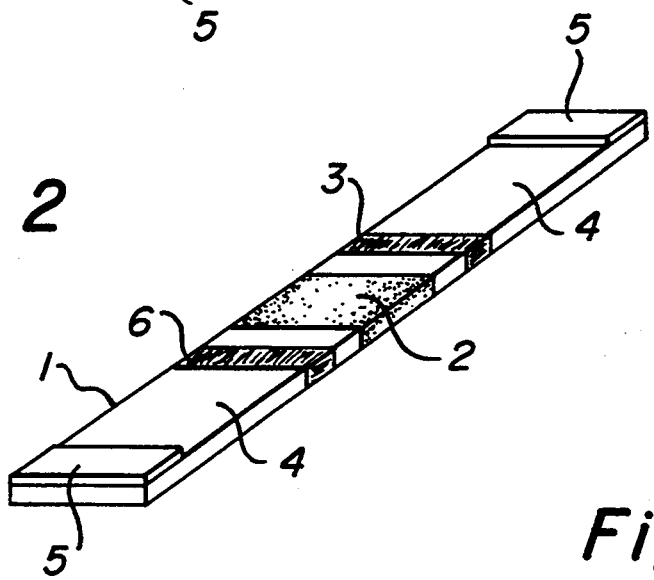
FIG. 2 shows a similar test strip where a control-detection zone (6) coated with antibodies to a labelled antibody used in the test is used instead of a streptavidin-coated measuring detection zone.
Figure 3A:
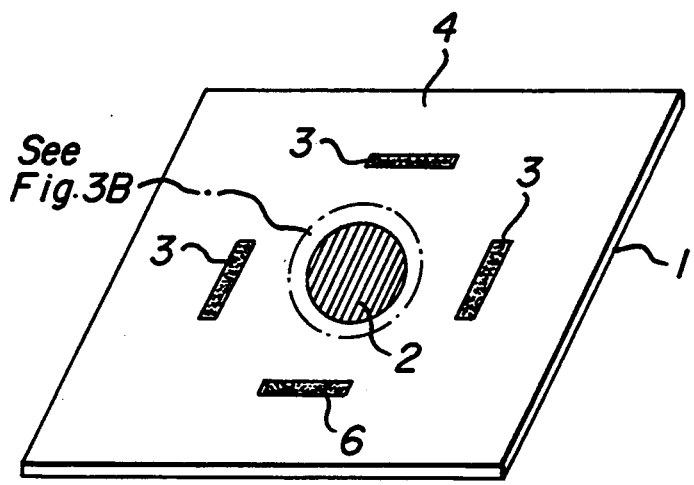
FIG. 3 shows an analysis element having a carrier (1) and a circular reaction zone (2) with micro-compartmentalized reagents A, B, C provided in the center thereof. Three measuring-reaction zones (3) and a control-detection zone (6) are provided around the reaction zone (2) while spaced apart therefrom at the same distance.
Figure 3B:

A: biotinylated T4-antibody ($5 \times 10^{-7}$M) in PBS buffer with 10 wt. % trehalose and 0.2 wt. % 8-anilino-1-naphthaline sulfonic acid (ANS).

B: T4-B-phycoerythrin (1:1, $10^{-6}$M in the above buffer)

C: Polystreptavidin (polymerized with bis-hydroxysuccinimide, average molecule seize <70 nm, 5 mg/ml in the above buffer)

Using a HEWLETT-PACKARD-PAINT-JET ™ multi-channel printer (Bubble-Jet), Reagents A and B are applied onto the center of a $4 \times 4$ cm² nitro-cellulose membrane (AES 98, manufactured by Schleicher und Schüle) according to the following line pattern:

---
— A
— B
— A
— B
---

The thickness of the line and the distance between the lines was approx. 250 μm.

The quantity of reagent applied was 0.5 μl/cm².

The lines covered a square of 0.7 cm in length.

This square served as the reaction zone.

Using a thin hollow needle (internal diameter 0.6 mm), reagent C was applied around the square formed by lines A and B so as to form a square with a length of 1.2 cm.

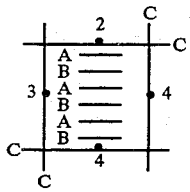

The dots 1-4 that are closest to the square formed by lines A and B are the 4 streptavidin-measuring-detection zones.

Test procedure

The membrane was placed in a support for a solid phase. 5 μl of an analyte sample (human serum) from a serum standard series were applied onto the center of the reaction zone. After 3 minutes, 3×15 μl washing buffer (PBS with 0.1 wt. %) TWEEN 20 ™ polyethoxysorbitan laurate surfactant were applied onto the center of the reaction zone in intervals of 15 seconds. After another 2 minutes, 3 of the 4 detection zones were measured using a Hitachi 4010 at Ex 515 nm, Em 580 nm.

The following are the results of the 5 analyses showing the measured results of three detection zones, the average values of these values and the values obtained for measuring only one detection zone.

| T4-concentration nmol/l | Fluorescence units | | | Mean value X (1, 2, 3) | Detection zone 1 |
|---|---|---|---|---|---|
| | Detection zone 1 | Detection zone 2 | Detection zone 3 | | |
| 0 | 0.47 | 0.57 | 0.54 | 0.53 | 0.56 |
| 47.6 | 0.43 | 0.38 | 0.42 | 0.41 | 0.43 |
| 94 | 0.34 | 0.33 | 0.28 | 0.32 | 0.27 |
| 175 | 0.25 | 0.22 | 0.22 | 0.23 | 0.23 |
| 328 | 0.14 | 0.17 | 0.20 | 0.17 | 0.20 |

The average value of the measured results of three detection zones produces an exactly uniform curve for different T4 concentrations where even T4 concentrations exceeding 100 mmol/l are clearly differentiated and are, hence, reproducible results.

Measuring series with only one measurement as a basis, however, produce curves with great deviations with partly poor differentiation for T4 concentrations over 100 mmol/l.

The contents of the following United States and foreign patent documents, which are discussed herein, are hereby incorporated by reference:

U.S. Pat. No. 4,361,537
U.S. Pat. No. 4,877,745
German Patent Application DE-A-4024544
German Patent Application DE-A-4024545
European Patent No. EP-A-0 291 194
European Patent No. EP-A-0 186 799
European Patent No. EP-A-0 344 578
European Patent No. EP-A-0 119 573
European Patent No. EP-A-0 268 237

We claim:

1. Analysis element for determination of an analyte in a sample liquid by a heterogeneous immunoassay, said element comprising:
a chromatographic porous carrier material having a reaction zone thereupon;
at least two spatially separated detection zones, wherein said detection zones are arranged around the reaction zone such that said detection zones are all adjacent to said reaction zone, and at least one absorptive zone provided adjacent the detection zones, facing away from the reaction zone, wherein said reaction zone comprises a plurality of soluble compartments which are close together and spatially separated, each of said compartments has one of an unlabelled analyte specific binding partner and a labelled binding partner which is a labelled analyte specific binding partner or a labelled analyte analogue therein, and wherein each detection zone comprises an immobilized specific binding reagent for one of said binding partners present on the reaction zone, and wherein at least one of said detection zones comprises a specific binding reagent for the unlabelled analyte specific binding partner.

2. Analysis element according to claim 1, wherein said at least two detection zones are provided at essentially the same distance from the reaction zone.

3. Analysis element according to claim 1, wherein the immobilized binding reagent for the analyte-specific binding partner is one of streptavidin and avidin.

4. Analysis element according to claim 1, wherein at least one of the detection zones contains a binding reagent for the labelled binding partner.

5. Analysis element according to claim 4, wherein the binding reagent for the labelled binding partner is an antibody.

6. Analysis element according to claim 1, wherein the compartments are spaced less than 1 mm apart from one another.

7. Analysis element according to claim 1, wherein the compartments of the reaction zone have a dimension of less than 2 mm in one surface direction.

8. Analysis element according to claim 7, wherein the dimension in one surface direction ranges from 15 μm to 1 mm.

9. Analysis element according to claim 1, wherein the compartments are configured to form lines.

10. Analysis element according to claim 1, wherein the compartments are configured to form dots.

11. Analysis element according to claim 1, wherein compartments containing identical reagents are separated from each other by compartments containing different reagents.

12. Analysis element according to claim 1, wherein the compartments of the reaction zone are applied with an ink-jet technique.

13. Analysis element according to claim 1, wherein the compartments of the reaction zone are applied with a bubble-jet technique.

14. Analysis element according to claim 1, wherein the compartments are applied with an air-brush technique.

15. A process for determination of an analyte in a sample liquid by a heterogeneous immunoassay, comprising the steps of:
providing an analysis element having a chromatographic porous carrier material having a reaction zone thereupon, with at least two spatially separated detection zones, wherein said detection zones are arranged around the reaction zone such that said detection zones are all adjacent to said reaction zone, and at least one absorptive zone provided adjacent the detection zones and facing away from the reaction zone, wherein said reaction zone comprises a plurality of soluble compartments which are close together and spatially separated, with each of the compartments having one of an unlabelled analyte specific binding partner and a labelled binding partner which is a labelled analyte specific binding partner or a labelled analyte analogue therein, and wherein each detection zone comprises an immobilized specific binding reagent for one of said binding partners present on the reaction zone, and wherein at least one of the detection zones comprises a binding reagent for the unlabelled analyte specific binding partner; said method further comprising the steps of applying a sample liquid onto said reaction zone;

applying a wash liquid onto the reaction zone such that dissolved reagents are, in a chromatographic process, transferred out of the reaction zone in a direction toward the detection zones;

measuring labelled reaction components bound in said detection zones, wherein measurement of one of said detection zones comprising a binding reagent for the unlabelled analyte specific binding partner is used for a first determination of the analyte in the sample, and measurement of one or more further detection zones is used for at least one of qualitative control and quantitative correction of the first determination.

16. Process according to claim 15, further comprising a step of determining a mean value from measurements obtained from at least two detection zones which contain a binding reagent for the unlabelled analyte-specific binding partner.

17. Process according to claim 16, wherein the measurements of at least two detection zones which contain a binding reagent for the unlabelled analyte-specific binding partner are carried out at different wavelengths.

18. Process according to claim 15, wherein measurements of at least one detection zone which contains a binding reagent for the labelled binding partner is used for positive reaction control.

19. Process according to claim 15, wherein measurements of at least one detection zone which contains a binding reagent for the labelled binding partner is used for quantitative correction of analyte determination.

20. Process according to claim 15, wherein the labelled binding partner is a labelled analyte or analyte analogue.

* * * * *